United States Patent [19]

Reinehr et al.

[11] 4,332,969
[45] Jun. 1, 1982

[54] SUBSTITUTED 11-AMINOUNDECANOLS

[75] Inventors: Dieter Reinehr, Kandern, Fed. Rep. of Germany; Adolf Hubele, Magden, Switzerland

[73] Assignee: Ciba-Geigy Corporation, Ardsley, N.Y.

[21] Appl. No.: 124,690

[22] Filed: Feb. 26, 1980

Related U.S. Application Data

[63] Continuation of Ser. No. 923,436, Jul. 10, 1978, abandoned.

[30] Foreign Application Priority Data

Jun. 19, 1977 [CH] Switzerland .................. 8914/77

[51] Int. Cl.³ ............... C07C 85/20; C07C 87/40; C07C 87/453; C07C 91/04
[52] U.S. Cl. ............... 564/460; 260/239 B; 564/279; 564/452; 564/453; 564/454; 564/457; 564/458; 564/462; 564/487; 564/502; 564/503; 424/325
[58] Field of Search ........... 260/584 R, 563 R, 563 C, 260/563 P

[56] References Cited

FOREIGN PATENT DOCUMENTS 2314697 10/1974 Fed. Rep. of Germany ... 260/584 R
2641448  3/1978 Fed. Rep. of Germany ... 260/584 R

OTHER PUBLICATIONS

Ruzicka et al., "Chem. Ab.", vol. 31, Ab. No. 3449⁸–3451³ (1937).
McKay et al., "Chem. Ab.", vol. 52, Ab. No. 10889h (1958).
Jasse, "Chem. Ab.", vol. 73, Ab. No. 131396p (1970).
Jasse, "Chem. Ab.", vol. 75, Ab. No. 152145n (1971).

*Primary Examiner*—John Doll
*Attorney, Agent, or Firm*—Michael W. Glynn

[57]     ABSTRACT

Novel substituted 11-aminoundecanols of the formula

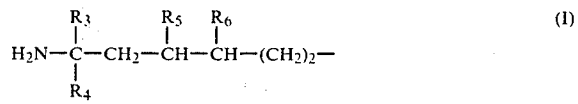

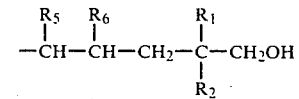

and a process for their preparation are described; in the formula, $R_1$ and $R_3$ independently of one another are hydrogen or alkyl having 1–8 C atoms and $R_2$ and $R_4$ independently of one another are alkyl having 1–8 C atoms, or $R_1$ and $R_2$ and/or $R_3$ and $R_4$ together with the bonding C atom form a cycloaliphatic ring having 4–8 C atoms, and $R_5$ and $R_6$ independently of one another are hydrogen or alkyl having 1–4 C atoms. The compounds of the formula I are valuable active compounds for combating plant pests.

8 Claims, No Drawings

SUBSTITUTED 11-AMINOUNDECANOLS

This is a continuation of application Ser. No. 923,436 filed on July 10, 1978, now abandoned.

The present invention relates to novel substituted 11-aminoundecanols, a process for their preparation and an agent for combating plant pests, which contains, as the active component, at least one 11-aminoundecanol according to the definition.

The novel 11-aminoundecanols are of the formula I

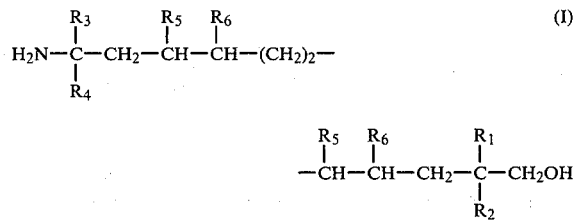

in which $R_1$ and $R_3$ independently of one another are hydrogen or alkyl having 1-8 C atoms and $R_2$ and $R_4$ independently of one another are alkyl having 1-8 C atoms, or $R_1$ and $R_2$ and/or $R_3$ and $R_4$ together with the bonding C atom form a cycloaliphatic ring having 4-8 C atoms, and $R_5$ and $R_6$ independently of one another are hydrogen or alkyl having 1-4 C atoms.

Compared with known amino-alcohols, especially unsubstituted 11-aminoundecanol, the compounds according to the invention are distinguished by an improved activity against plant pests, especially phytopathogenic fungi.

The compounds of the formula I can be prepared in a simple manner by converting a 1-aza-1,5,9-cyclododecatriene of the formula II

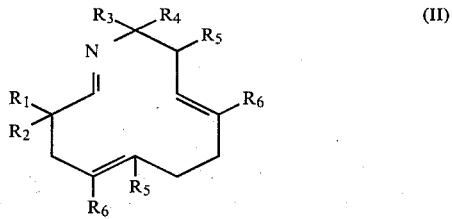

in which $R_1$ to $R_6$ are as defined under formula I, in an aqueous or aqueous-organic medium in the presence of an inorganic acid which is non-oxidising under the reaction conditions, to a compound of the formula III

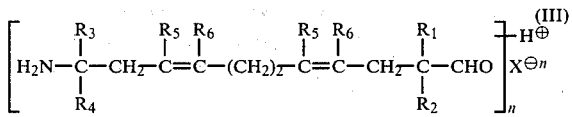

in which $R_1$ to $R_6$ are as defined under formula I, X is the anion of an inorganic acid which is non-oxidising under the reaction conditions and n is an integer corresponding to the valency of X, and then catalytically hydrogenating the compound of the formula III to give a compound of the formula I.

Alkyl groups $R_1$ to $R_6$ can be straight-chain or branched. Alkyl groups $R_1$ to $R_3$ preferably have 1-5 C atoms and alkyl groups $R_4$ preferably have 1-7 C atoms. Examples of alkyl groups $R_1$ to $R_6$ are: the methyl, ethyl, n-propyl, isopropyl, n-, sec.- and tert.-butyl, n-pentyl, 2- or 3-pentyl, n-hexyl, 3-heptyl and n-octyl group.

If $R_1$ and $R_2$ and/or $R_3$ and $R_4$ together with the bonding C atom form a cycloaliphatic ring, this is in particular an unsubstituted cycloalkyl ring having 5–8 C atoms. Preferably, the said substituents, together with the bonding C atom, form a cyclopentyl or cyclohexyl group.

Preferred 11-aminoundecanols of the formula I are those in which $R_5$ and $R_6$ are each hydrogen, $R_1$ and $R_3$ independently of one another are hydrogen or alkyl having 1–5 C atoms, $R_2$ is alkyl having 1–5 C atoms and $R_4$ is alkyl having 1–7 C atoms, or in which $R_3$, $R_5$ and $R_6$ are each hydrogen, $R_1$ and $R_2$ together with the bonding C atom are cyclopentyl or cyclohexyl and $R_4$ is alkyl having 1–7 C atoms.

Particularly preferred compounds of the formula I are those in which $R_3$, $R_5$ and $R_6$ are each hydrogen, $R_1$ and $R_2$ independently of one another are alkyl having 1–4 C atoms, especially methyl, ethyl, n-propyl and n-butyl, or together with the bonding C atom are cyclohexyl, and $R_4$ is alkyl having 1–7 C atoms, especially ethyl, isopropyl, tert.-butyl, 2- or 3-pentyl or 3-heptyl.

The hydrolysis of the compounds of the formula II in the presence of an inorganic, non-oxidising acid is carried out according to the definition in an aqueous or aqueous-organic medium. Examples of suitable organic solvents are alcohols, especially those having 1–4 C atoms, aliphatic diols, for example 1,2-ethanediol, 1,3-propanediol and 1,4-butanediol, and cyclic ethers, for example tetrahydrofuran, tetrahydropyran and dioxan. The hydrolysis is preferably carried out in an aqueous medium.

Inorganic acids which are non-oxidising under the reaction conditions and can be used for the hydrolysis are, for example, hydrogen halide acids, such as HCl and HBr, sulphuric acid, phosphoric acid, dilute nitric acid and perchloric acid. Preferably, the hydrolysis is carried out in the presence of sulphuric acid.

The compound of the formula II and the non-oxidising inorganic acid are employed in at least the stoichiometric amount. Preferably, however, an excess of acid is used, for example an up to ten-fold excess and in particular an up to about three-fold excess.

The hydrolysis is generally carried out at temperatures between about 0° and 60° C., preferably between about 20° and 40° C. The salts of the formula III obtained after the hydrolysis can, if desired, be isolated in a manner known per se, for example by evaporating the reaction solution. However, such isolation is generally not necessary.

Hydrogenation catalysts which are known per se can be employed for the hydrogenation of the salts of the formula III to the 11-aminoundecanols of the formula I. These catalysts can be used in the conventional forms, for example as finely divided powders, in colloidal form or in the form of oxides or hydroxides, or applied to suitable supports, such as asbestos, pumice, kieselguhr, silica gel, silica or activated charcoal. Particularly suitable catalysts are noble metal catalysts, such as platinum, rhodium, palladium, ruthenium and iridium catalysts, in particular platinum-on-charcoal and palladium-on-charcoal catalysts.

The reaction temperatures for the hydrogenation are advantageously between about 0° and 100° C. Hydrogenation temperatures between about 20° and 50° C. are preferred.

The hydrogenation can be carried out in an aqueous or aqueous-organic medium. Organic solvents which can be used are those of the type mentioned in the context of the hydrolysis. Preferably, the hydrogenation is carried out in an aqueous medium. Since intermediate isolation of the salts of the formula III is not necessary, both the hydrolysis and the subsequent hydrogenation can advantageously be carried out in the same reaction medium.

The hydrogenation can be carried out at normal pressure or under an excess pressure of up to about 100 atmospheres. The reaction is preferably carried out at normal pressure or under an excess pressure of up to about 10 atmospheres.

After the reaction has ended, the catalysts are removed, the reaction solution is neutralised and the compounds of the formula I are isolated in a manner known per se, for example by means of distillation and, if desired, prior extraction.

The starting compounds of the formula II can be prepared by reacting an aza-butadiene of the formula IV

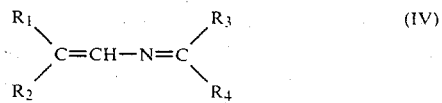

in the presence of a catalyst which is obtained by reducing a carbonyl-free nickel compound in the presence of a chelating olefin and if desired in the presence of an electron donor, at temperatures between about −40° C. and +150° C. with a compound of the formula V

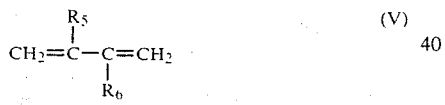

in which formulae $R_1$ to $R_6$ are as defined under formula I. Suitable catalysts are described, for example, in German Offenlegungsschrift No. 2,330,087.

Preferred catalysts are those obtained in situ by reducing a carbonyl-free nickel compound such as nickel stearate and in particular nickel acetylacetonate, with halogen-free metal-aryls or metal-alkyls, for example ethoxy-diethyl-aluminium, in the presence of an alkyl- or aryl-phosphine or in the presence of an alkyl phosphite or aryl phosphite. The diolefins of the formula V are known. The aza-butadienes of the formula IV are known in some cases and can be prepared, for example, as follows:

By reacting ketones of the formula

with allylamine to give aza-butadienes of the formula IV in which $R_1$ is hydrogen and $R_2$ is methyl and $R_3$ and $R_4$ are as defined. With this process, in the main compounds of the formula VI

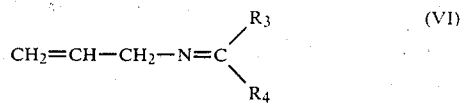

are first formed and these can be isomerised in the presence of suitable catalysts, such as $K_2O/Al_2O_3$ catalysts, at elevated temperatures to give aza-butadienes of the formula IV in which $R_1$ to $R_4$ are as defined above.

By reacting aldehydes of the formula

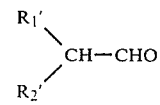

in which $R_1'$ and $R_2'$ are alkyl groups having 1–8 C atoms or together with the bonding C atom are a cycloaliphatic ring having 4–8 C atoms, with ammonia to give compounds of the formula VII

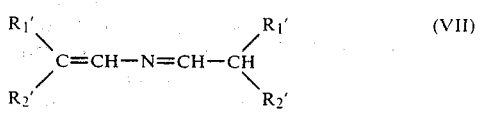

and, if desired, further reacting the compounds of the formula VII with suitable aldehydes or ketones.

By isomerising compounds of the formula VIIIa or VIIIb

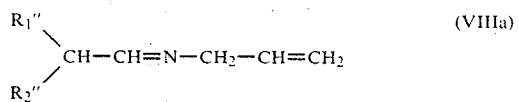

or

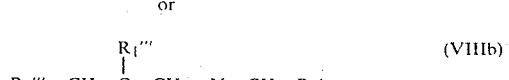

in which $R_1''$ and $R_2''$ independently of one another are alkyl having 1–8 C atoms, or together with the bonding C atom are a cycloaliphatic ring having 4–8 C atoms, $R_1'''$ is hydrogen or alkyl having 1–8 C atoms, $R_2'''$ is hydrogen or alkyl having 1–7 C atoms and $R_4'$ is tertiary alkyl having 4–8 C atoms, at temperatures between about 0° and 80° C., preferably about 10°–50° C., in the presence of an inert organic solvent, for example anhydrous benzene or toluene, and in the presence of an alkali metal alcoholate or alkaline earth metal alcoholate, such as sodium tert.-butylate or potassium tert.-butylate.

When compounds of the formula VIIIa are used, azabutadienes of the formula IV are formed in which $R_1$ and $R_2$ independently of one another are alkyl having 1–8 C atoms, or together with the bonding C atom are a cycloaliphatic ring having 4–8 C atoms, $R_3$ is hydrogen and $R_4$ is ethyl. When compounds of the formula VIIIb are used, on the other hand, aza-butadienes of the formula IV are obtained in which $R_1$ is hydrogen or alkyl having 1–8 C atoms, $R_2$ is alkyl having 1–8 C atoms, $R_3$ is hydrogen and $R_4$ is tertiary alkyl having 4–8 C atoms.

The compounds of the formula VIIIa or VIIIb can, in turn, be prepared in a manner known per se, by reacting aldehydes

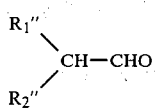

with allylamine or, respectively, by reacting an amine of the formula

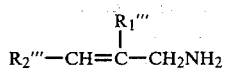

with an aldehyde of the formula $R_4'$-CHO.

The compounds of the formula I are valuable active compounds for combating plant pests. Using the active compounds of the formula I, fungi arising on plants or parts of plants (fruit, blossoms, foliage, stems, tubers and roots) can be controlled or destroyed and even parts of plants which grow subsequently remain immune to fungi of this type. The compounds of the formula I thus also have a preventive action. They are active, for example, against the phythopathogenic fungi belonging to the following classes: Basidiomycetes, such as, in particular, rust fungi (Puccinia and others); *Fungi imperfecti* (for example Cercospora) and Phycomycetes (for example Oomycetes, such as Plasmopara and Phytophthora). They can also be used as dressings for treating seeds (fruit, tubers and grain) and plant cuttings to protect them against fungus infections, and also against phytopathogenic fungi occurring in soil. Examples of cultivated plants to be protected are: cereals, maize, rice, vegetables, sugar beet, soya, groundnuts, fruit trees, ornamental plants, vines, hops, cucurbitaceae (cucumber, marrow and melons), potatoes, tobacco, tomatoes and also banana plants, cocoa plants and natural rubber plants.

2,2-Dimethyl-11-ethyl-11-undecanol has a particularly good activity.

The compounds of the formula I can be used on their own or together with suitable carriers and/or other additives. Suitable carriers and additives can be solid or liquid and correspond to the substances customary in formulation technology, for example natural or regenerated mineral substances, solvents, dispersants, wetting agents, adhesives, thickeners, binders and fertilisers.

The content of active ingredient in marketable agents is between 0.1 and 90 percent by weight.

For application, the compounds of the formula I can be in the following processing forms, the percentage data given in brackets indicating advantageous amounts of active ingredient.

Solid processing forms: dusting agents and sprinkling agents (up to 10% by weight), granules, coated granules, impregnated granules and homogeneous granules and pellets (grains) [1 to 80% by weight];

Liquid processing forms: (a) active ingredient concentrates which are dispersible in water: wettable powders and pastes (25–90% by weight in the commercial pack, 0.01 to 15% by weight in the ready-to-use solution); emulsion concentrates and solution concentrates (10 to 50% by weight in concentrates; 0.01 to 15% by weight in the ready-to-use solution); and (b) solutions (0.1 to 20% by weight) and aerosols.

In order to broaden the biological spectrum of action desired in practice, the active substances of the formula I can be employed together with further fungicides, bactericides, herbicides, insecticides, acaricides, nematicides and/or rodenticides and also with fertilisers and other plant nutrients or plant growth regulators.

The active ingredients of the formula I of the present invention can be formulated, for example, as follows (%=percent by weight):

Dusting agents

The following substances are used to prepare (a) a 5% dusting agent and (b) a 2% dusting agent:

| (a) | 5 parts of active ingredient and 95 parts of talc; |
|---|---|
| (b) | 2 parts of active ingredient, 1 part of highly disperse silica and 97 parts of talc. |

The active ingredients are mixed and ground with the carrier substances and can be used in this form as a dust.

Granules

The following substances are used to prepare 5% granules:

5 parts of active ingredient,
0.25 part of epichlorohydrin,
0.25 part of cetyl polyglycol ether,
3.50 parts of polyethylene glycol and
91 parts of kaolin (grain size 0.3–0.8 mm).

The active substance is mixed with epichlorohydrin and the mixture is dissolved in 6 parts of acetone, and polyethylene glycol and cetyl polyglycol ether are then added. The solution thus obtained is sprayed onto kaolin and the acetone is then evaporated in vacuo.

Wettable powders

The following constituents are used to prepare (a) a 70% wettable powder, (b) a 40% wettable powder, (c) and (d) 25% wettable powders and (e) a 10% wettable powder:

(a) 70 parts of active ingredient,
5 parts of sodium dibutylnaphthylsulphonate,
3 parts of a 3:2:1 naphthalenesulphonic acids/phenolsulphonic acids/formaldehyde condensation product,
10 parts of kaolin and
12 parts of Champagne chalk;

(b) 40 parts of active ingredient,
5 parts of the sodium salt of ligninsulphonic acid,
1 part of the sodium salt of dibutylnaphthalenesulphonic acid and
54 parts of silica;

(c) 25 parts of active ingredient,
4.5 parts of calcium ligninsulphate,
1.9 parts of a 1:1 mixture of Champagne chalk/hydroxyethylcellulose,
1.5 parts of sodium dibutyl-naphthalenesulphonate,
19.5 parts of silica,
19.5 parts of Champagne chalk and
28.1 parts of kaolin;

(d) 25 parts of active ingredient,
2.5 parts of isooctylphenoxy-polyoxyethyleneethanol,
1.7 parts of a 1:1 mixture of Champagne chalk/hydroxyethylcellulose,
8.3 parts of sodium aluminium silicate,
16.5 parts of kieselguar and
46 parts of kaolin;

(e) 10 parts of active ingredient,
3 parts of a mixture of the sodium salts of saturated fatty alcohol sulphates, -continued .5 parts of a naphthalenesulphonic acid/formaldehyde condensation product and
82 parts of kaolin.

The active ingredients are intimately mixed with the additives in suitable mixers and ground in appropriate mills and rollers. Wettable powders of outstanding wettability and outstanding suspension properties are obtained and these can be diluted with water to give suspensions of the desired concentration and can be used in particular for leaf application.

Emulsifiable concentrates

The following substances are used to prepare a 25% emulsifiable concentrate:

25 parts of active ingredient,
2.5 parts of epoxidised vegetable oil,
10 parts of an alkylarylsulphonate/fatty alcohol polyglycol ether mixture,
5 parts of dimethylformamide and
57.5 parts of xylene.

Emulsions of the desired concentration can be prepared from such concentrates by dilution with water and these emulsions are particularly suitable for leaf application.

The compounds of the formula I can also be used as active ingredients for regulating plant growth.

A. PREPARATION EXAMPLES

Example 1

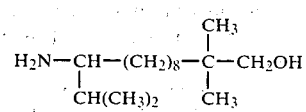

(a)
3,3-Dimethyl-12-isopropyl-1-aza-1,5,9-cyclododecatriene

Under a blanketing gas (argon), 2.57 g (0.01 mol) of nickel acetylacetonate and 1.66 g (0.01 mol) of triethyl phosphite are dissolved in 120 g of absolute toluene, after which the solution is saturated at 20°–25° C. with 1,3-butadiene. 3.9 g (0.03 mol) of ethoxydiethylaluminium are then slowly added dropwise, whilst passing in a gentle stream of 1,3-butadiene, and during the addition the original green colour changes in the course of 5 minutes to light red. The reaction mixture is heated to 60° C. and 122.5 g (0.98 mol) of N-isobutylidene-2-methylpropenylamine [prepared by reacting isobutyraldehyde with ammonia in accordance with J. Org. Chem., 26, 1822-25 (1961); boiling point 139°–141° C./760 mm Hg] are added dropwise in the course of 45 minutes, whilst passing in a vigorous stream of 1,3-butadiene, at such a rate that the butadiene passed in is just consumed. After the dropwise addition has ended, the mixture is stirred for a further 1 hour at 60° C. whilst continuously passing in 1,3-butadiene, and is then cooled to 20°–25° C. In order to deactivate the catalyst, 0.32 g (0.01 mol) of sulphur is added to the reaction solution and the solution is distilled. A first fraction, which in addition to 120 g of toluene also contains traces of triethyl phosphite and butadiene dimers (gas chromatogram), is obtained at a bath temperature of up to 50° C./1 mm Hg. Subsequent fine distillation yields 212.5 g (0.912 mol) of 3,3-dimethyl-12-isopropyl-1-aza-1,5,9-cyclododecatriene; yield 93% of theory, based on converted N-isobutylidene-2-methylpropenylamine (conversion 100%); boiling point 54°–55° C./0.01 mm Hg; $n_D^{20} = 1.4832$.

(b) 2,2-Dimethyl-11-isopropyl-11-aminoundecanol 218 g (0.935 mol) of 3,3-dimethyl-12-isopropyl-1-aza-1,5,9-cyclododecatriene are added dropwise in the course of 15 minutes to a solution of 150 g (1.53 mols) of sulphuric acid in one liter of water. Aldehyde impurities are removed by a subsequent 20 minute steam distillation. The aqueous sulphuric acid solution is then hydrogenated at normal pressure and 20°–25° C. in the presence of a platinum-on-charcoal catalyst (5% by weight of platinum), with the absorption of 3 mols of hydrogen, to give 2,2-dimethyl-11-isopropyl-11-aminoundecanol. After filtering off the catalyst, the aqueous solution is neutralised with concentrated sodium hydroxide solution and the oily amino-alcohol which separates out is extracted by shaking with toluene and distilled. 196 g (0.763 mol) of 2,2-dimethyl-11-isopropyl-11-aminoundecanol are obtained, corresponding to a yield of 81.5% of theory; boiling point 110° C./0.02 mm Hg; $n_D^{20} = 1.4684$.

Analysis for $C_{16}H_{35}NO$ (molecular weight 257): Calculated: C, 74.64%; H, 13.70%; N, 5.44%. Found: C, 74.8%; H, 13.5%; N, 5.5%.

Mass spectrum: molecular peak 257, fragment masses 242, 226, 214, 196, 154 and 72.

$^1$H-NMR spectrum $\tau$(ppm): 6.76(s), 7.50(m), 8.30(s), 8.4–8.8(m), 9.05(d) and 9.12(s) in a ratio of 2:1:2:18:12.

IR spectrum (liquid): $\nu$(OH) 3,350 cm$^{-1}$; $\delta$(NH$_2$) 1,585 cm$^{-1}$; $\delta$(CH$_3$) 1,380 and 1,365 cm$^{-1}$.

Example 2

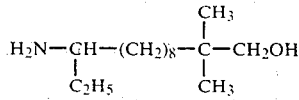

(a)
3,3-Dimethyl-12-ethyl-1-aza-1,5,9-cyclododecatriene

The procedure described in Example 1 (a) is essentially repeated except that 48.5 g (0.437 mol) of N-propylidene-(2-methylpropenylamine) [1-ethyl-4,4-dimethyl-2-aza-1,3-butadiene] and 61.0 g (1.13 mols) of 1,3-butadiene are used and 2.8 g of triphenylphosphine are used in place of triphenyl phosphite. Distillation yields 62.0 g (0.283 mol) of 3,3-dimethyl-12-ethyl-1-aza-1,5,9-cyclododecatriene; boiling point 65°–66° C./0.005 mm Hg; $n_D^{20} = 1.4864$.

The N-propylidene-(2-methyl-propenylamine) used in the above example was prepared as follows: 25 g (0.223 mol) of potassium tert.-butylate are suspended in one liter of anhydrous diethyl ether. 921 g (8.3 mols) of isobutylidene-allylamine are then added dropwise in the course of 1 hour, with continuous stirring, at such a rate that the temperature of the reaction mixture does not rise above 20° C. After the dropwise addition is complete, the mixture is stirred for a further 5 hours at 20°–22° C. The reaction is then discontinued and the solvent is distilled over at a bath temperature of 40° C. and under a pressure of 200–50 mm Hg. The residue is distilled at a bath temperature of 70° C./0.1 mm Hg into a receiver cooled with CO₂/methanol. Subsequent fine distillation yields 808 g (7.93 mols) of N-propylidene(2-methylpropenylamine); boiling point 122° C.; $n_D^{20} = 1.471$.

(b) 2,2-Dimethyl-11-ethyl-11-aminoundecanol

The procedure described in Example 1 (b) is repeated except that 199 g (0.91 mol) of 3,3-dimethyl-12-ethyl-1-aza-1,5,9-cyclododecatriene are used. Distillation yields 149 g (0.613 mol) of 2,2-dimethyl-11-ethyl-11-aminoundecanol, corresponding to a yield of 67.4% of theory; boiling point 118° C./0.05 mm Hg; $n_D^{20} = 1.4656$.

Analysis for $C_{15}H_{33}NO$ (molecular weight 243): Calculated: C, 74.01%; H, 13.64%; N 5.76%. Found: C, 73.84%; H, 13.92%; N 5.73%.

Mass spectrum: molecular peak 243, fragment masses 213, 193, 182 and 140.

¹H-NMR spectrum τ(ppm): 6.78(s), 7.47(m), 7.88(s), 8.4–8.9(m), 9.14(t) and 9.18(s) in a ratio of 2:1:2:19:9.

IR spectrum (liquid): ν(OH) 3,330 cm⁻¹; δ(NH₂) 1,590 cm⁻¹; δ(CH₃) 1,377 and 1,360 cm⁻¹.

Example 3

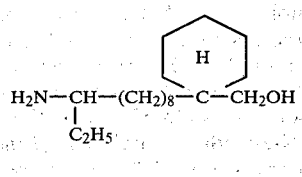

(a) 3-Spiro-cyclohexane-12-ethyl-1-aza-1,5,9-cyclododecatriene

The procedure described in Example 1 (a) is essentially repeated except that 2.8 g of triphenylphosphine, 109 g (0.72 mol) of propylidene-(cyclohexylidenemethylamine) and 123 g (2.28 mols) of 1,3-butadiene are used. Distillation yields 115 g (0.444 mol) of 3-spiro-cyclohexane-12-ethyl-1-aza-1,5,9-cyclododecatriene; boiling point 103° C./0.03 mm Hg; $n_D^{20} = 1.5101$.

The propylidene-(cyclohexylidenemethylamine) used in the above example was prepared analogously to the N-propylidene-(2-methylpropenylamine) according to Example 2 (a) except that 5 g of potassium tert.-butylate, 240 g (1.59 mols) of cyclohexyl-methylidene-allylamine and 250 ml of tetrahydrofuran were used. After a reaction time of 1 hour at 30° C., 199 g (1.32 mols) of propylidene(cyclohexylidenemethylamine) are obtained; boiling point 51°–53° C./0.3 mm Hg; $n_D^{20} = 1.5072$.

(b) 2-Spiro-cyclohexane-11-ethyl-11-aminoundecanol

The procedure described in Example 1 (b) is repeated except that 20 g (0.077 mol) of 3-spiro-cyclohexane-12-ethyl-1-aza-1,5,9-cyclododecatriene and 15 g (0.153 mol) of sulphuric acid are used. Distillation yields 12.5 g (0.044 mol) of 2-spiro-cyclohexane-11-ethyl-11-aminoundecanol, corresponding to a yield of 57.1% of theory; boiling point 140° C./0.03 mm Hg; $n_D^{20} = 1.4902$.

Analysis for $C_{18}H_{37}NO$ (molecular weight 283): Calculated: C, 76.26%; H, 13.15%; N, 4.93%; O 5.64%. Found: C, 76.5%; H, 12.9%; N, 5.0%; O 5.7%.

Mass spectrum (Cl/CH₄): M+H (peak) 284, MH-H₂O=266.

¹H-NMR spectrum τ(ppm): 6.59(s), 7.34(m), 8.4–8.7(m) and 9.03(t) in a ratio of 2:1:31:3.

IR spectrum (liquid): τ(OH) 3,300 cm⁻¹; δ(NH₂) 1,595 cm⁻¹; δ(CH₃) 1,375 cm⁻¹.

Example 4

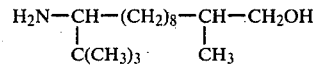

(a) 3-Methyl-12-tert.-butyl-1-aza-1,5,9-cyclododecatriene

The procedure described in Example 1 (a) is essentially repeated except that 2.8 g of triphenylphosphine, 160 g (1.28 mols) of N-2,2-dimethylpropylidene-(propenylamine) and 120 g (2.22 mols) of 1,4-butadiene are used. After a reaction time of 6 hours at 42° C., distillation yields 161 g (0.69 mol) of 3-methyl-12-tert.-butyl-1-aza-1,5,9-cyclododecatriene; boiling point 65° C./0.05 mm Hg; $n_D^{20} = 1.4866$.

The N-2,2-dimethylpropylidene-(propenylamine) used in the above example was prepared analogously to the N-propylidene-(2-methylpropenylamine) according to Example 2 (a) except that 10 g of potassium tert.-butylate, 330 g (2.95 mols) of (2,2-dimethyl-propylidene)-allylamine and 450 ml of benzene were used. After a reaction time of 3.5 hours at 40° C., 325 g (2.9 mols) of N-2,2-dimethylpropylidene-(propenylamine) are obtained as a mixture of the cis/trans isomers in a weight ratio of 65:35; boiling point 110° C.; $n_D^{20} = 1.4487$.

(b) 2-Methyl-11-tert.-butyl-11-aminoundecanol

The procedure described in Example 1 (b) is repeated except that 116 g (0.497 mol) of 3-methyl-12-tert.-butyl-1-aza-1,5,9-cyclododecatriene are used. Distillation yields 22 g (0.0856 mol) of 2-methyl-11-tert.-butyl-11-aminoundecanol, corresponding to a yield of 17.3% of theory; boiling point 110° C./0.02 mm Hg; $n_D^{20} = 1.4649$.

Analysis for $C_{16}H_{35}NO$ (molecular weight 257): Calculated: C, 74.64%; H, 13.70%; N, 5.44%; O 6.21%. Found: C, 74.73%; H, 13.69%; N, 5.48%; O 6.19%.

Mass spectrum: no molecular peak, fragment masses 242, 200, 182 and 86.

¹H-NMR spectrum τ(ppm): 6.56(dd), 7.65(d), 8.52(s), 8.69(s), 9.07(d) and 9.10(s) in a ratio of 2:1:3:17:12.

IR spectrum (liquid): ν(OH) 3,300 cm⁻¹; δ(NH₂) 1,600 cm⁻¹; δ(CH₃) 1,390 and 1,360 cm⁻¹.

Example 5

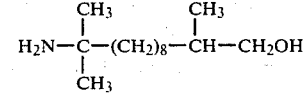

(a) 3,12,12-Trimethyl-1-aza-1,5,9-cyclododecatriene

The procedure described in Example 1 (a) is essentially repeated except that 2.8 g of triphenylphosphine, 110 g (1.13 mols) of N-isopropylidene-propenylamine [prepared by reacting acetone with allylamine; cf. B. A. Kazanskii et al., Zhurnal Organicheskoi Khimii, Volume 6, No. 11, 2197–9 (1970)] and 108 g (2 mols) of 1,3-butadiene are used. Distillation yields 187.0 g (0.91 mol) of 3,12,12-trimethyl-1-aza-1,5,9-cyclododecatriene; boiling point 66° C./0.03 mm Hg; $n_D^{20}=1.4895$.

(b) 2,11,11-Trimethyl-11-aminoundecanol

The procedure described in Example 1 (b) is repeated except that 200 g (0.975 mol) of 3,12,12-trimethyl-1-aza-1,5,9-cyclododecatriene are used. Distillation yields 20.5 g (0.0895 mol) of 2,11,11-trimethyl-11-aminoundecanol, corresponding to a yield of 9.2% of theory; boiling point 103° C./0.05 mm Hg; $n_D^{20}=1.4645$.

Analysis for $C_{14}H_{31}NO$ (molecular weight 229): Calculated: C, 73.30%; H 13.62%; N, 6.11%; O 6.98%. Found: C, 73.58%; H 13.66%; N, 6.27%; O 7.24%.

Mass spectrum: molecular peak 229, fragment masses 214, 140 and 58.

$^1$H-NMR spectrum $\tau$(ppm): 6.60(dd), 8.25(s), 8.69(s) and 9.07(d) in a ratio of 2:3:17:6:3.

IR spectrum (liquid): $\nu$(OH) 3,300 cm$^{-1}$; $\delta$(NH$_2$) 1,600 cm$^{-1}$; $\delta$(CH$_3$) 1,380 and 1,365 cm$^{-1}$; $\nu$(C—OH) 1,050 cm$^{-1}$.

Example 6

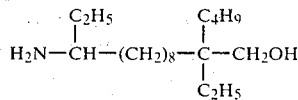

(a) 3,12-Diethyl-3-n-butyl-aza-1,5,9-cyclododecatriene

The procedure described in Example 1 (a) is essentially repeated except that 467 g (2.8 mols) of N-propylidene-(2-ethylhexen-1-yl-amine), 324 g (6 mols) of 1,3-butadiene, 15.7 g (1 mmol) of nickel acetylacetonate, 7.45 g (60 mmols) of trimethyl phosphite, 23.4 g (180 mmols) of ethoxy-diethyl-aluminium and 300 ml of toluene are used. After a reaction time of 4 hours at 40° C., working up as described in Example 1 (a) yields 624 g (2.27 mols) of 3,12-diethyl-3-n-butyl-1-aza-1,5,9-cyclododecatriene as a mixture of isomers; yield 81% of theory, based on the converted N-propylidene-(2-ethyl-hexen-1-yl-amine) (conversion 100%); boiling point 98°–100° C./0.3 mm Hg; $n_D^{20}=1.4905$.

The N-propylidene-(2-ethylhexen-1-yl-amine) used in the above example was prepared analogously to the N-propylidene-(2-methylpropenylamine) according to Example 2 (a) except that 10 g of potassium tert.-butylate, 800 g (4.79 mols) of (2-ethylhexylidene)-allylamine and 600 ml of tetrahydrofuran were used. After a reaction time of 2 hours at 35° C., 682 g (4.08 mols) of N-propylidene-(2-ethyl-hexen-1-yl-amine) are obtained, corresponding to a yield of 85.2% of theory (mixture of isomers in a weight ratio of 55:45); boiling point 53°–56° C./1 mm Hg; $n_D^{20}=1.4698$.

(b) 2,11-Diethyl-2-n-butyl-11-aminoundecanol

The procedure described in Example 1 (b) is repeated except that 138 g (0.501 mol) of 3,12-diethyl-3-n-butyl-1-aza-1,5,9-cyclododecatriene are used. Distillation yields 45 g (0.151 mol) of 2,11-diethyl-2-n-butyl-11-aminoundecanol, corresponding to a yield of 30.1% of theory; boiling point 138°–142° C./0.01 mm Hg; $n_D^{20}=1.471$.

Analysis for $C_{19}H_{41}NO$ (molecular weight 299.54): Calculated: C, 76.19%; H, 13.80%; N, 4.68%; O 5.34%. Found: C, 76.30%; H, 13.94%; N, 4.76%; O 5.48%.

Mass spectrum: molecular peak 299 (300=M+H and 298=M−H), fragment masses 280, 270, 268, 252, 200 and 128.

IR spectrum (liquid): $\nu$(OH) 3,250 cm$^{-1}$; $\delta$(NH$_2$) 1,595 cm$^{-1}$; $\delta$(CH$_3$) 1,375 cm$^{-1}$; $\nu$(C—O) 1,045 cm$^{-1}$.

$^1$H-NMR spectrum $\tau$(ppm): 6.69(s), 7.4(m), 8.32(s), 8.5–8.9(m) and 9.0–9.3(m) in a ratio of 2:1:2:27:9.

Example 7

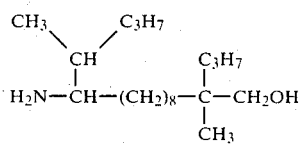

(a) 3-Methyl-3-n-propyl-12-(2-pentyl)-1-aza-1,5,9-cyclododecatriene

Analogously to Example 6(a), 710 g (3.93 mols) of N-2-methylpentylidene-(2-methyl-penten-1-yl-amine) [prepared by reacting 2-methylvaleraldehyde with ammonia in accordance with U.S. Pat. No. 2,319,848] and 432 g (8.0 mols) of 1,3-butadiene are reacted. After working up the reaction mixture, 995 g (3.45 mols) of 3-methyl-3-n-propyl-12-(2-pentyl)-1-aza-1,5,9-cyclododecatriene are obtained as a mixture of isomers (two main isomers); yield 87.7% of theory, based on converted N-2-methyl-pentylidene-(2-methyl-penten-1-yl-amine) (conversion 100%); boiling point 103°–105° C./0.3 mm Hg; $n_D^{20}=1.4886$.

(b) 2-Methyl-2-n-propyl-11-(2-pentyl)-11-aminoundecanol

The procedure described in Example 1 (b) is repeated except that 145 g (0.52 mol) of 3-methyl-3-n-propyl-12-(2-pentyl)-1-aza-1,5,9-cyclododecatriene are used. Distillation yields 52 g (0.168 mol) of 2-methyl-2-n-propyl-11-(2-pentyl)-11-aminoundecanol, corresponding to a yield of 32% of theory; boiling point 142°–144° C./0.01 mm Hg; $n_D^{20}=1.4706$.

Analysis for $C_{20}H_{43}NO$ (molecular weight 313.57): Calculated: C, 76.61%; H, 13.82%; N, 4.47%; O 5.10%. Found: C, 76.35%; H, 13.70%; N, 4.57%; O 5.24%.

Mass spectrum: no molecular peak (312=M−H), fragment masses 282, 242, 224 and 210.

$^1$H-NMR spectrum $\tau$(ppm): 6.70(s), 7.4(m), 8.45(s) and 8.75(m) and 9.13(m) in a ratio of 2:1:28:12.

IR spectrum (liquid): $\nu$(OH) 3,300 cm$^{-1}$; $\delta$(NH$_2$) 1,600 cm$^{-1}$; $\delta$(CH$_3$) 1,375 cm$^{-1}$; $\nu$(C—O) 1,053 cm$^{-1}$.

Example 8

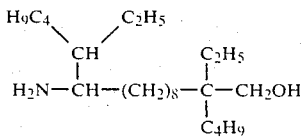

(a) 3-Ethyl-3-n-butyl-12-(3-heptyl)-1-aza-1,5,9-cyclododecatriene

The procedure described in Example 6 (a) is repeated except that 760 g (3.21 mols) of N-2-ethyl-hexylidene(2-ethyl-hexen-1-yl-amine) [prepared by reacting 2-ethylcaproaldehyde with ammonia in accordance with U.S. Pat. No. 2,319,848] and 378 g (7 mols) of 1,3-butadiene are used. After working up the reaction mixture, 930 g (2.69 mols) of 3-ethyl-3-n-butyl-12-(3-heptyl)-1-aza-1,5,9-cyclododecatriene are obtained as a 7:3 mixture of isomers; this corresponds to a yield of 84% of theory, based on converted N-2-ethyl-hexylidene-(2-ethyl-hexen-1-yl-amine) (conversion 100%); boiling point 106°–109° C./0.1 mm Hg; $n_D^{20}=1.4895$.

(b) 2-Ethyl-3-n-butyl-11-(3-heptyl)-11-aminoundecanol

The procedure described in Example 1 (b) is repeated except that 84.1 g (0.241 mol) of 3-ethyl-3-n-butyl-12-(3-heptyl)-1-aza-1,5,9-cyclododecatriene are used. Distillation with a molecular distillation unit (heating temperature=180° C., oil pump vacuum=0.02 mm Hg) yields 43 g (0.117 mol) of 2-ethyl-3-n-butyl-11-(3-heptyl)-11-aminoundecanol, corresponding to a yield of 48.5% of theory; $n_D^{20}=1.4803$.

Analysis for $C_{24}H_{51}NO$ (molecular weight 369.68): Calculated: C, 77.98%; H, 13.91%; N, 3.79%; O 4.33%. Found: C, 72.26%; H, 13.94%; N, 3.76%; O 4.37%.

Mass spectrum: molecular peak 369 (370=M+H and 368=M−H), fragment masses 338, 270, 252, 238 and 128.

$^1$H-NMR spectrum $\tau$(ppm): 6.67(s), 7.26(m), 8.7(m) and 9.1(m) in a ratio of 2:1:36:12.

IR spectrum (liquid): $\nu$(OH) and $\nu(NH_2)$ 3,300 cm$^{-1}$; $\delta(NH_2)$ 1,595 cm$^{-1}$; $\delta(CH_3)$ 1,375 cm$^{-1}$; $\nu$(C—O) 1,045 cm$^{-1}$.

Example 9

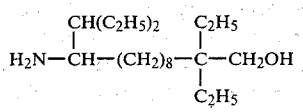

(a) 3,3-Diethyl-12-(3-pentyl)-1-aza-1,5,9-cyclododecatriene

The procedure described in Example 1 (a) is repeated except that 3.4 g (0.011 mol) of triphenyl phosphite, 72.4 g (0.4 mol) of 1-(3-pentyl)-4,4-diethyl-2-aza-1,3-butadiene [prepared by reacting 2-ethyl-butyraldehyde with ammonia in accordance with U.S. Pat. No. 2,319,848] and 48.4 g (0.895 mol) of 1,3-butadiene are used. Working up as described in Example 1 (a) yields 56.8 g (0.197 mol) of 3,3-diethyl-12-(3-pentyl)-1-aza-1,5,9-cyclododecatriene, corresponding to a yield of 51.2% of theory, based on converted 1-(3-pentyl)-4,4-diethyl-2-aza-1,3-butadiene (conversion 96.4%); boiling point 90°–92° C./10$^{-3}$ mm Hg; $n_D^{20}=1.4840$.

(b) 2,2-Diethyl-11-(3-pentyl)-11-aminoundecanol

The procedure described in Example 1 (b) is repeated except that 85 g (0.294 mol) of 3,3-diethyl-12-(3-pentyl)-1-aza-1,5,9-cyclododecatriene are used. Distillation yields 25 g (0.08 mol) of 2,2-diethyl-11-(3-pentyl)-11-aminoundecanol, corresponding to a yield of 27.2% of theory; boiling point 136°–138° C./0.03 mm Hg; $n_D^{20}=1.4545$.

Analysis for $C_{20}H_{43}NO$ (molecular weight 313.57): Calculated: C, 76.61%; H, 13.82%; N, 4,47%; O 5.10%. Found: C, 76.94%; H, 14.04%; N, 4.32%; O 5.00%.

Mass spectrum: molecular peak 313, fragment masses 282, 242, 224 and 212.

$^1$H-NMR spectrum $\tau$(ppm): 6.68(s), 7.28(m), 8.5–8.9(m) and 9.0–9.2(m) in a ratio of 2:1:28:12.

IR spectrum (liquid): $\nu$(OH) and $\nu(NH_2)$ 3,300 cm$^{-1}$; $\delta(NH_2)$ 1,590 cm$^{-1}$; $\delta(CH_3)$ 1,377 cm$^{-1}$; $\nu$(C—O) 1,048 cm$^{-1}$.

B. USE EXAMPLES

1. Action against *Cercospora personata* (=*C. arachidicola*) on groundnut plants 3-week old groundnut plants were sprayed with a spray liquor (0.02% of active substance) prepared from a wettable powder of the active ingredient. After about 12 hours, the treated plants were dusted with a conidia suspension of the fungus. The infected plants were then incubated for about 24 hours at >90% relative atmospheric humidity and then placed in a greenhouse at about 22° C. The fungus infection was evaluated after 12 days. Compared with an untreated control, plants which were treated with active ingredients of the formula I, for example the compound according to Preparation-Example 2, had a slight or virtually no fungus infection.

2. Action against *Puccinia graminis f. sp. sccalis* on *Secale cereale*

Residual protective action 4 days after sowing, rye plants were sprayed with a spray liquor (0.06% of active substance) prepared from a wettable powder of the active ingredient. After 24 hours, the treated plants were infected with a uredospore suspension of the fungus. After incubating for 48 hours at 95–100% relative atmospheric humidity and about 20° C., the infected plants were placed in a greenhouse at about 22° C. An evaluation of the rust pustule development was made 12 days after the infection. Compared with control plants which were untreated but infected, the infection with rust fungus was greatly inhibited or completely controlled with compounds of the formula I, for example the compound according to Preparation Example 3.

3. Action against Phytophthora infestans on tomatoes

Curative action

After cultivating for three weeks, tomato plants of the "Rotor Gnom" variety were sprayed with a zoospore suspension of the fungus and incubated in a cabin at 18° to 20° C. and saturated atmospheric humidity. Humidification was interrupted after 24 hours. After drying, the plants were sprayed with a liquor which contained the active substance, formulated as a wettable powder, in a concentration of 0.06%. After the spray coating had dried on, the plants were again placed in the humid cabin for 4 days. The number and size of the typical leaf spots arising after this time were used as the evaluation scale for the effectiveness of the substances tested. In this test the compound according to Preparation Example 1, for example showed a good action.

What is claimed is:

1. A compound of the formula

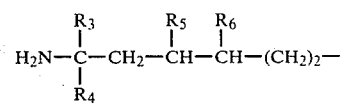

-continued

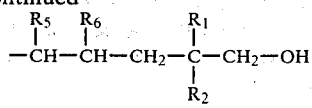

in which $R_3$, $R_5$ and $R_6$ are each hydrogen, $R_1$ and $R_2$ independently of one another are alkyl having 1–4 C atoms or together with the bonding C atom are cyclohexyl and $R_4$ is alkyl having 1–7 C atoms.

2. A compound according to claim 1, which is 2,2-dimethyl-11-isopropyl-11-aminoundecanol.

3. A compound according to claim 1, which is 2,2-dimethyl-11-ethyl-11-aminoundecanol.

4. A compound according to claim 1, which is 2-spirocyclohexane-11-ethyl-11-aminoundecanol.

5. A compound according to claim 1, which is 2-methyl-2-n-propyl-11-(2-pentyl)-11-aminoundecanol.

6. A compound which is 2,11,11-trimethyl-11-aminoundecanol.

7. A process for the preparation of a compound of formula I

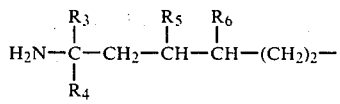 (I)

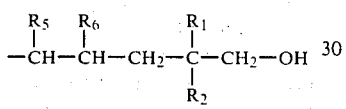

in which $R_1$ and $R_3$ independently of one another are hydrogen or alkyl having 1–8 C atoms and $R_2$ and $R_4$ independently of one another are alkyl having 1–8 C atoms, or $R_1$ and $R_2$ and/or $R_3$ and $R_4$ together with the bonding C atom form a cycloaliphatic ring having 4–8 C atoms, and $R_5$ and $R_6$ independently of one another are hydrogen or alkyl having 1–4 C atoms, which comprises converting a 1-aza-1,5,9-cyclododecatriene of the formula II

 (II)

in an aqueous or aqueous-organic medium in the presence of an inorganic acid which is non-oxidising under the reaction conditions, to a compound of the formula III

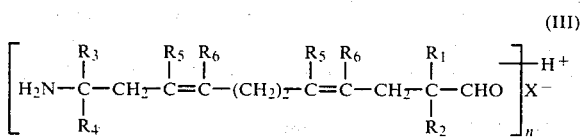 (III)

in which X is the anion of an inorganic acid which is nonoxidising under the reaction conditions and n is an integer corresponding to the valency of X, and then catalytically hydrogenating the compound of the formula III to give a compound of the formula I.

8. A process according to claim 7, which comprises carrying out the conversion of a compound of the formula II to a compound of the formula III in an aqueous medium in the presence of sulphuric acid.

* * * * *